US00PP11237P

United States Patent [19]

Pieters

[11] Patent Number: Plant 11,237

[45] Date of Patent: Feb. 22, 2000

[54] CHRYSANTHEMUM PLANT NAMED 'GEDI VER'

[76] Inventor: Dirk Pieters, Schierveldstraat 3A, Oosnieuwkerke, 8840 Staden, Belgium

[21] Appl. No.: 09/124,808

[22] Filed: Jul. 29, 1998

[51] Int. Cl.[7] ..... A01H 5/00

[52] U.S. Cl. ..... Plt./295

[58] Field of Search ..... Plt./295

[56] References Cited

U.S. PATENT DOCUMENTS

| | | | |
|---|---|---|---|
| P.P. 6,156 | 4/1988 | Hesse | Plt./295 |
| P.P. 8,610 | 2/1994 | VandenBerg | Plt./295 |
| P.P. 8,611 | 2/1994 | VandenBerg | Plt./295 |
| P.P. 9,370 | 11/1995 | VandenBerg | Plt./295 |

*Primary Examiner*—Howard J. Locker
*Attorney, Agent, or Firm*—Christie, Parker & Hale, LLP

[57] ABSTRACT

A new plant variety of Chrysanthemum producing yellow anemone-type flowers.

2 Drawing Sheets

BACKGROUND OF THE INVENTION

The present invention is directed to a new and distinct variety of Chrysanthemum plant botanically classified as *Dendranthema grandiflora*. The varietal denomination of the new chrysanthemum is 'GEDI VER'.

The female parent of the new variety is the variety known as 'Ballino' and the male parent is a variety known as 'Leyla'. The new variety has been asexually reproduced by vegetative cuttings in Ventura County, Calif. and the distinguishing characteristics are retained through successive generations of asexual reproduction.

SUMMARY OF THE INVENTION

'GEDI VER' is a pot type Chrysanthemum plant variety that produces small yellow anemone-type flowers.

COMPARISON WITH PARENTS

'GEDI VER' differs from both parents in flower form. Whereas the new variety is anemone type, the parent flowers are daisy type. Flower diameter is also smaller than both parents and the plant shape is more uniform.

BRIEF DESCRIPTION OF ILLUSTRATIONS

The accompanying photographs show typical specimens of the plant and flowers of the new variety with colors being as nearly true as possible with illustrations of this type.

DESCRIPTION OF THE PLANT

Figure 1:
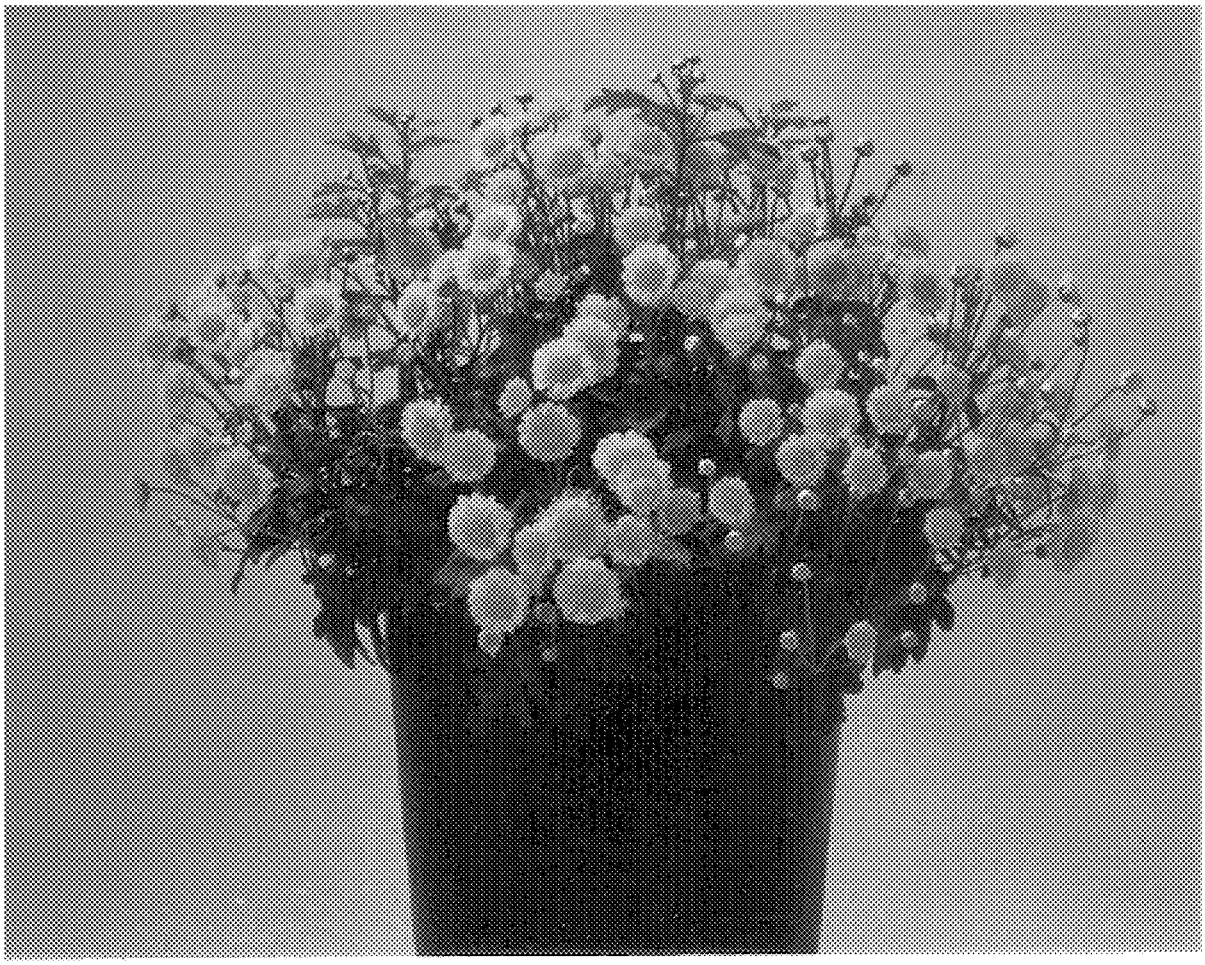
FIG. 1 is a whole plant view of the new cultivar grown in a pot.
Figure 2:
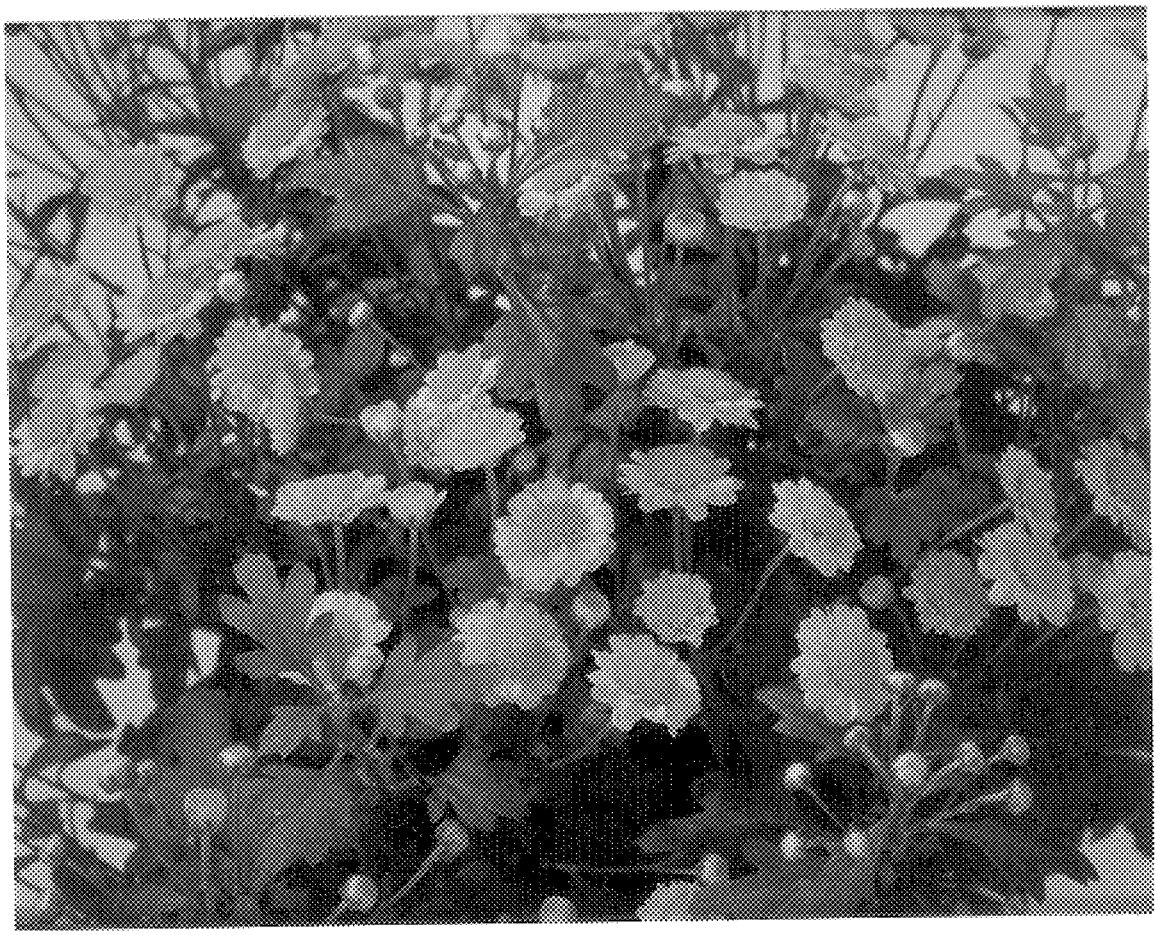
FIG. 2 is a closer view, showing inflorescence and foliage characteristics of the new cultivar in greater detail.

The following description of the new variety is of specimens grown in a greenhouse in Ventura County, Calif. in the month of April. 'GEDI VER' has not been observed under all possible environmental conditions. The phenotype may vary with variations in the environment such as temperature, light intensity, day length and cultural conditions. The color designations herein are from The Royal Horticultural Society Colour Chart except where general terms are used.

To produce a commercial product the plants may be pinched once about ten days after planting. It has been observed that the shelf life of 'GEDI VER' is about 29 days with the response time of about 7 weeks. No growth regulator treatment was used on plants described. Useful growing conditions include night temperatures of about 18°–20° C., day temperatures of about 20°–30° C. and about 5,000 to 6,000 foot-candles of light. The new variety blooms naturally in September in Ventura County, Calif.

Plant:

*Habit.*—Mounding herbaceous perennial, free branching.
*Height.*—About 29 cm.
*Number of breaks from pinch.*—About 6.
*Length of lateral branches.*—About 24 cm.
*Stem color.*—Near 146C.

Foliage:

*Leaf arrangement.*—Alternate.
*Number of leaves per lateral branch.*—About 18 fully expanded leaves.
*Leaf size.*—Length: About 5.8 cm. Width: About 3.5 cm.
*Leaf shape.*—Ovate.
*Attachment.*—Petioled.
*Leaf apex.*—Acuminate.
*Base.*—Tapered.
*Margin.*—Palmately lobed.
*Aspect.*—Slightly undulating.
*Surface.*—Top: Lightly pubescent. Bottom: Lightly pubescent.
*Venation.*—Prominent on underside. Color: Underside: Near 137D. Upperside: Near 146C.
*Petiole.*—Length: About 1.6 cm. Color: Near 144A.
*Color.*—Mature leaf: Top: Near 137B. Bottom: Near 137C. Young leaf: Top: Near 137B. Bottom: Near 147B.

Bloom:

*Inflorescence form.*—Cyme, sub-erect.
*Bloom form.*—Anemone.
*Number of blooms per branch.*—Average 21.
*Diameter of fully expanded bloom.*—About 1.6 cm.
*Depth of fully expanded bloom.*—About 0.8 cm.
*Sepal number.*—About 20. Color: Near 137B.
*Peduncle.*—Length: Terminal: About 3.5 cm. Lateral: About 6 cm. Habit: Straight. Surface: Lightly pubescent. Color: Near 144A.
*Flower bud* (*when just showing color*).—Color: Near 6B. Diameter: About 0.7 cm. Height: About 0.5 cm. Shape: Flattened sphere.

*Ray florets.*—Number per flower: Average 42. Texture: Matte. Shape: Ovate. Apex: 2 to 3 obtuse lobes. Base: Tapered. Margin: Entire. Aspect: Slightly recurved. Length: About 1 cm. Width: About 0.4 cm.

*Disc florets.*—Number per flower: About 80. Texture: Matte. Shape: Cylindric, fluted apex. Length: About 0.6 cm. Width: About 0.15 cm.

*Fragrance.*—Faint.

Flower color:

*General flower description.*—Bright yellow anemone with orange/yellow center.

*Ray florets, top side.*—Immature: Near 9B. Mature: Near 12B. Fading: Near 13C.

*Ray floret, under side.*—Immature: Near 9B. Mature: Near 6B. Fading: Near 6C.

*Disc florets.*—Immature: Near 13B.

What is claimed is:

1. A new and distinct Chrysanthemum plant of the variety substantially as herein shown and described.

* * * * *